United States Patent
Misra

[11] Patent Number: 4,975,461
[45] Date of Patent: Dec. 4, 1990

[54] P-AMINOPHENOLS, DERIVATIVES THEREOF AND METHOD OF USE

[75] Inventor: Raj N. Misra, Hopewell, N.J.

[73] Assignee: E. R. Squibb & Sons, Inc., Princeton, N.J.

[21] Appl. No.: 876,053

[22] Filed: Jun. 19, 1986

[51] Int. Cl.$^5$ .............................................. A61K 31/05
[52] U.S. Cl. .................................... 514/510; 260/404; 514/617; 514/629; 514/657; 514/826; 514/63; 560/139; 564/222; 564/428
[58] Field of Search ................ 560/139; 514/625, 657, 514/510, 629, 826, 863, 617; 564/428, 222; 260/404

[56] References Cited

U.S. PATENT DOCUMENTS 3,819,637  6/1974  Bell .
4,510,139  4/1985  Bailey .................................. 514/234
4,515,980  11/1983  Drug .

FOREIGN PATENT DOCUMENTS 79141  10/1981  European Pat. Off. .
81321  6/1983  European Pat. Off. .
122518  10/1984  European Pat. Off. .

OTHER PUBLICATIONS

Vanhoof et al, Chemical Abstracts, 75:76463x 6-1971.
Vanhoof et al, Chemical Abstracts, 88:190458t 10-1977.
Pless et al, Chemical Abstracts, 100:51307w 7-1983.
Hey, Lawton Soc. 1940 384, 387.
I. G. Farbenind, D.R.P. 530825 [1926]; Frdl. 18 604.
I. G. Farbenind, Schweiz.P. 135643 [1927].
I. G. Farbenind, D.R.P. 642549.
Borsche, Hahn, B. 82 [1949]260, 262.
Burcherer, Stohmann, C. 1904 I, 1012-Blattchen.

"Antiinflammatory 2-(Aminomethyl)Phenols. Structure-Activity Relationship", Itoh et al.
"Biochemical and Pharmacological Activities of Ono-3122, A Diuretic, and Ono-3144, A Novel Anti--Inflammatory Drug", Aishita et al.
Jambuservala, Holt, Mason, Soc. 1931 373, 375.
I. G. Farbenind, D.R.P. 580519 ]1932 ; Frdl. 20 490.
Kehrmann, Neil, B. 47, 3102-Krystalle (aus Benzol).

*Primary Examiner*—Werren B. Lone
*Attorney, Agent, or Firm*—Burton Rodney

[57] ABSTRACT p-Aminophenols are provided having the structure

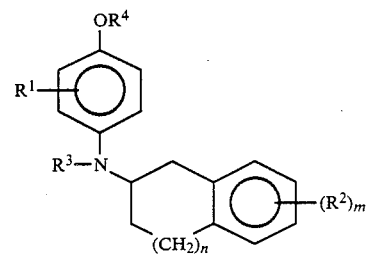

wherein m is 0, 1 or 2; n is 0, 1, 2 or 3; $R^1$ and $R^2$ may be the same or different and are H, hydroxy or alkoxy; $R^3$ is H, lower alkyl, alkanoyl or aroyl and $R^4$ is H, lower alkyl or alkanoyl, and including acid-addition salts thereof.

These compounds are useful as inhibitors of leukotriene production and as such are useful as antiallergy, anti-inflammatory and anti-psoriatic agents.

18 Claims, No Drawings

P-AMINOPHENOLS, DERIVATIVES THEREOF AND METHOD OF USE

DESCRIPTION OF THE INVENTION

The present invention relates to p-aminophenols and derivatives thereof which prevent leukotriene formation in macrophages and as such are useful, for example, as antiallergy agents, anti-inflammatory agents and in the treatment of psoriasis. These compounds have the structural formula

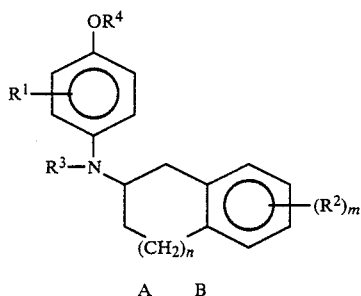

wherein m is 0, 1 or 2; n is 0, 1, 2 or 3; $R^1$ and $R^2$ may be the same or different and may be H, hydroxy, or alkoxy; $R^2$ may be a substituent on either or both the A ring or B ring (with the B ring being preferred); $R^3$ is H, lower alkyl, alkanoyl or aroyl; and $R^4$ is H, lower alkyl or alkanoyl, and including pharmaceutically acceptable salts thereof.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids, (e.g., hydrochloric and hydrobromic acid), sulfuric acid, nitric acid and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic or methanesulfonic.

In addition, a method is provided for treating asthma mediated by leukotrienes in a mammalian species in need of such treatment, which method includes the step of administering to a mammalian host an effective amount of a compound of formula I or a pharmaceutically acceptable salt thereof.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups and/or 1 or 2 hydroxy groups.

The term "aralkyl", "aryl-alkyl" or "aryl-lower alkyl" as used herein refers to lower alkyl groups as discussed above having an aryl substituent, such as benzyl.

The term "halogen" or "halo" as used herein refers to chlorine, bromine, fluorine or iodine with chlorine being preferred.

The terms "alkanoyl" and "aroyl" refer to a lower alkyl group linked to a carbonyl

group and an aryl group linked to a carbonyl group, respectively.

The terms "lower alkoxy", "alkoxy", "aralkoxy", "alkanoyloxy", and "aroyloxy" include any of the above lower alkyl, aralkyl, alkanoyl and aroyl groups linked to an oxygen atom.

The term $(CH_2)_n$ includes straight or branched chain radicals having from 0 to 3 carbons in the normal chain. Examples of $(CH_2)_n$ groups include

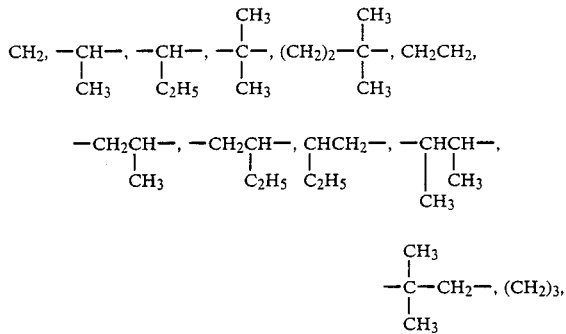

and the like.

Preferred compounds of the invention or for use in the method of the invention are those compounds wherein n is 0 or 1, m is 1 or 2, $R^1$ is H, $R^4$ is H or alkanoyl, $R^3$ is H or alkyl, $R^2$ is in the B ring and is H, OH or alkoxy.

The various compounds of the invention or compounds used in the method of the invention may be prepared as described below.

In general, indane and tetralin substituted p-aminophenols in accordance with the present invention are prepared by reductive amination of the appropriate indanones or tetralones with commercially available 4-benzyloxyaniline hydrochloride followed by removal of the benzyl protecting group, in accordance with the following reaction sequence.

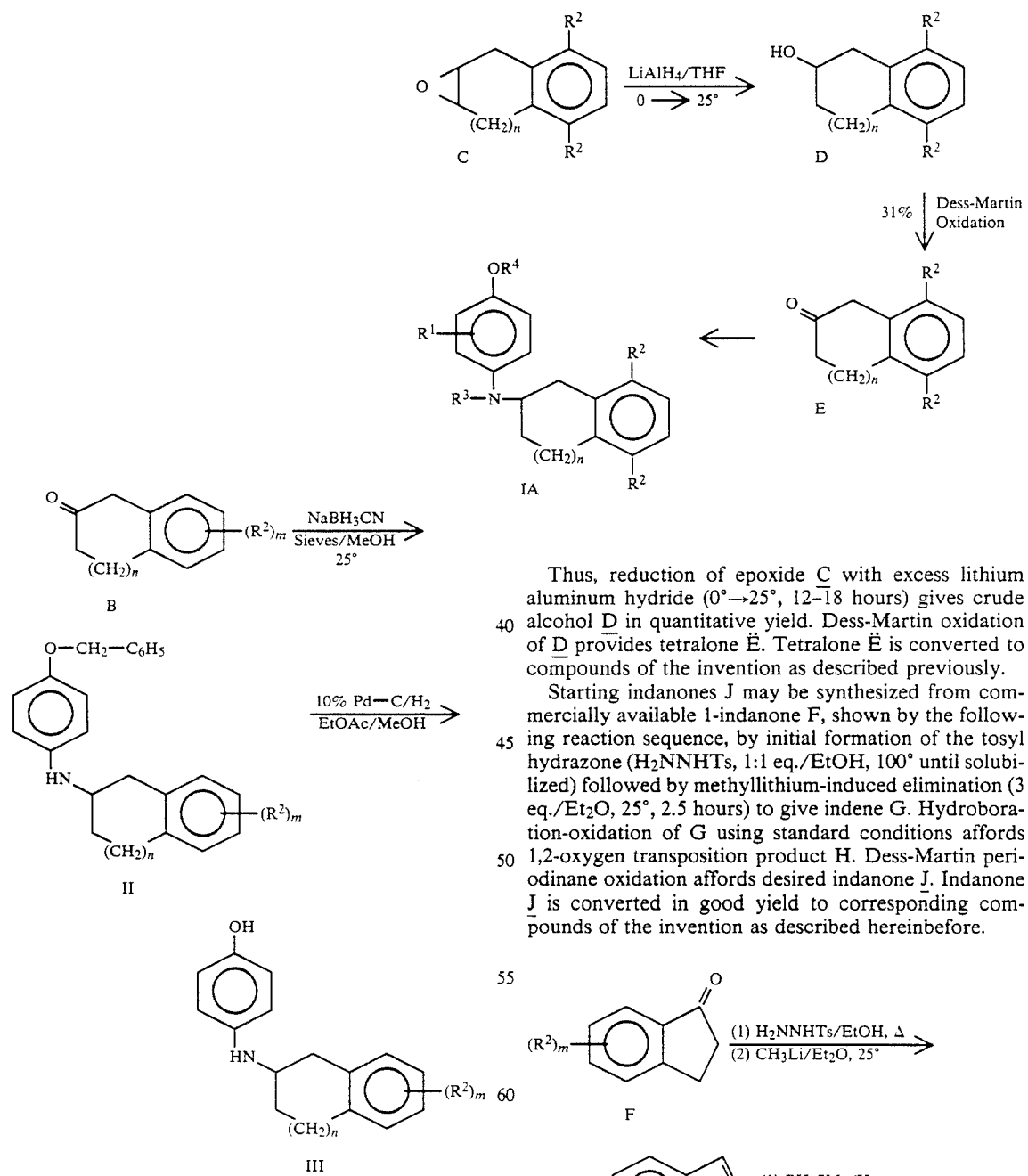

reactions are generally complete in 2-4 hours at room temperature. Hydrogenolysis (10% Pd-C/H₂, 1 atm./EtOAc/MeOH) affords the desired N-substituted-p-aminophenols in good yields when a ~1:10 (w/w) ratio of catalyst to substrate is employed. Increasing the ratio of catalyst to substrate gives substantially lower yields.

The requisite indanone and tetralone precursor $\underline{B}$ wherein $R^2$ is alkoxy, such as methoxy in the $\overline{6}$ or $\overline{7}$ position, or is H are commercially available.

The tetralone precursor wherein $R^2$ is in the 5,8-positions are prepared from epoxide $\underline{C}$ as shown in the following sequence.

Thus, reduction of epoxide $\underline{C}$ with excess lithium aluminum hydride (0°→25°, 12–18 hours) gives crude alcohol $\underline{D}$ in quantitative yield. Dess-Martin oxidation of $\underline{D}$ provides tetralone $\underline{\ddot{E}}$. Tetralone $\underline{\ddot{E}}$ is converted to compounds of the invention as described previously.

Starting indanones J may be synthesized from commercially available 1-indanone F, shown by the following reaction sequence, by initial formation of the tosyl hydrazone (H₂NNHTs, 1:1 eq./EtOH, 100° until solubilized) followed by methyllithium-induced elimination (3 eq./Et₂O, 25°, 2.5 hours) to give indene G. Hydroboration-oxidation of G using standard conditions affords 1,2-oxygen transposition product H. Dess-Martin periodinane oxidation affords desired indanone $\underline{J}$. Indanone $\underline{J}$ is converted in good yield to corresponding compounds of the invention as described hereinbefore.

The procedure employed involves stirring the ketone and amine hydrochloride Ä (1.0–1.5 equivalents) over 3 Å molecular sieves in methanol with excess sodium cyanoborohydride (1.5–3.0 hydride equivalents). The -continued

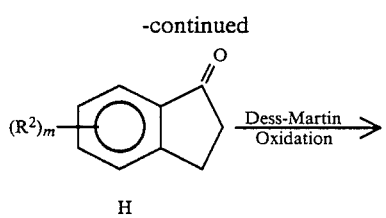
H

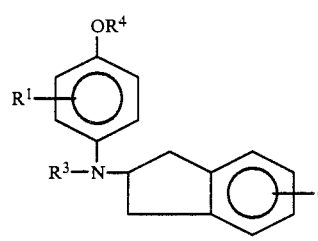
J

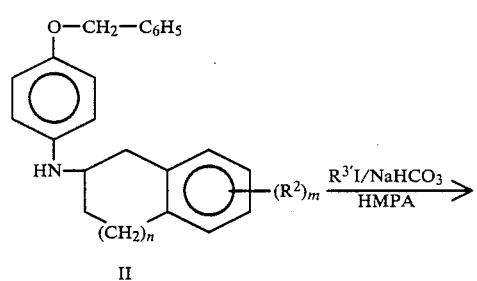
ID

Ester IG is prepared as shown below from the substituted benzyloxyaniline intermediate II. Reaction of this intermediate II with an iodide $R^{3'}$ I (wherein $R^{3'}$ is alkyl, aroyl or alkanoyl) (1.25–1.5 eg./NaHCO$_3$/HMPA, 25°, 2–4 hours) gives IE. Removal of the benzyl protecting group from IE affords aminophenols IF cleanly by TLC. The crude oils are esterified with the appropriate acid chloride (1.1 eq./CH$_2$Cl$_2$, 0°, 15 minutes) using 1.1 equivalents of 4-dimethylaminopyridine as a catalyst/base.

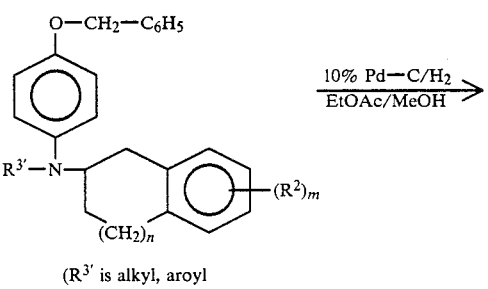
II

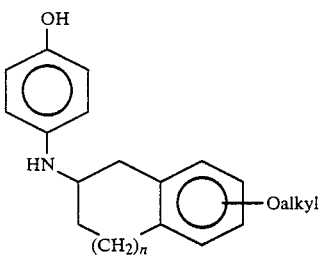
($R^{3'}$ is alkyl, aroyl or alkanoyl)
IE

-continued

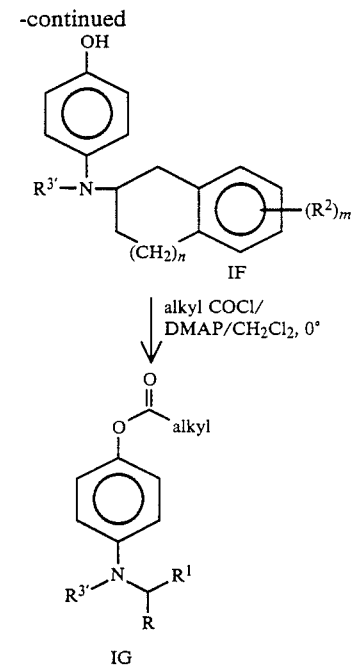
IF

IG

Compounds of formula I wherein $R^2$ is OH may be prepared directly from compounds of the structure III by demethylation with boron tribromide (3 eq., $-78° \rightarrow 25°$ then three hours).

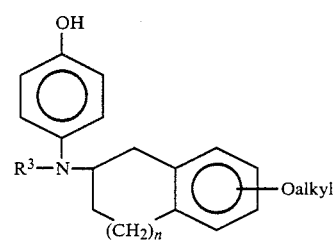
III

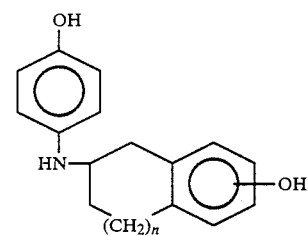
IV

Compounds of formula I wherein $R^2$ is alkoxy may be prepared directly from compounds of the structure IV by alkylating IV by treating with an alkyl halide in the presence of base such as sodium hydride to form V

V

Where R[4] in the compounds of the invention is other than H, the starting compounds wherein R[4] is H may be alkylated directly to form the formula IIIA compound

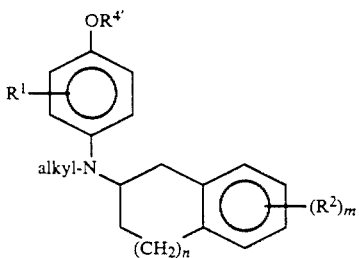

IIIA (where R[4'] is alkyl, alkanoyl or aroyl)

The compounds of the invention are inhibitors and prevent leukotriene formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma, inflammation and psoriasis.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol.

EXAMPLE 1

4-[(1,2,3,4-Tetrahydro-2-naphthalenyl)amino]phenol

A.

4-Benzyloxy-N-(1,2,3,4-tetrahydro-2-naphthalenyl)aniline

A solution of 1.00 g (4.2 mmol, Aldrich) of 4-benzyloxyaniline hydrochloride, 560 μl (4.24 mmol, Aldrich) of β-tetralone and 132 mg (2.10 mmol) of sodium cyanoborohydride in 30 ml of MeOH over 3A molecular sieves was stirred at room temperature for 2.5 hours. The mixture was filtered, EtOAc was added and this was washed with saturated NaHCO$_3$ twice. The organic layer was dried (MgSO$_4$) and concentrated in vacuo. Purification via flash chromatography (silica gel, 1:10 EtOAc/petroleum ether) afforded 1.28 g (93%) of title compound as a golden yellow oil.

IR(Film): 3399, 3062, 3017, 2925, 1510, 1453, 1229, 1026, 817, 750 cm$^{-1}$; 270 MHz $^1$H NMR(CDCl$_3$)

δ 1.70 (m, 1H, cyclohexyl H)
2.12 (m, 1H, cyclohexyl H)
2.67 (dd, J=8, 16, 1H, cyclohexyl H)
2.87 (dd, J̄=6, 6, 2H, cyclohexyl H's)
3.16 (dd, J̄=b 4, 16, 1H, cyclohexyl H)
3.69 (br s, 1H, methine)
4.97 (s, 2H —CH$_2$Ph)
6.58 (d, J=9 Hz, 2H, phenol H's)
6.84 (d, J̄=9 Hz, 2H, phenol H's)
7.14 (m, 4H, aromatic H's of tetralone)
7.34 (m, 6H, phenuyl H's and NH)

TLC: Rf (1:2 EtOAc/petroleum ether)=0.59, UV and PMA, homogeneous.

B. 4-(1,2,3,4-Tetrahydro-2-naphthalenyl)-amino]phenol

A solution of 1.26 g (3.84 mmol) of Part A compound and 380 mg of 10% palladium on carbon in 20 ml of MeOH and 5 ml of EtOAc was stirred at room temperature under a hydrogen atmosphere (balloon) for 24 hours. The reaction mixture was filtered through a small column of Celite, eluted with EtOAc and the filtrate concentrated in vacuo. Purification via flash chromatography (silica gel, 1:3 EtOAc/petroleum ether) and then recrystallization (EtOAc/petroleum ether) afforded mg (20%) of the title compound as a white solid: m. p. 169°–170° C.

IR(KBr): 3411, 3276, 2930, 1494, 1385, 1226, 1139, 1079, 826, 741 cm$^{-1}$; 270 MHz $^1$H NMR (DMSO-d$_6$)

δ 1.53 (m, 1H, cyclohexyl H)
2.06 (m, 1H, cyclohexyl H)
2.61 (dd, J=8, 16, 1H, cyclohexyl H)
2.84 (crude t, 2H, cyclohexyl H's)
3.03 (dd, J=4, 16, 1H, —NH—CH)
4.78 (br s, 1H, —NH— or —OH)
6.49 (d, J=8 Hz, 2H phenol H's)
6.55 (d, J̄=8 Hz, 2H, phenol H's)
7.06 (s, 4H, aromatic H's of the tetralone)
8.36 (s, 1H, —NH or —OH)
MS(CI): 240 (M+H)$^+$ TLC: Rf (silica gel, 1:2 EtOAc/petroleum ether)=0.20, UV and PMA, homogeneous.

Microanalysis Calc'd for C$_{16}$H$_{17}$NO:
Calc'd: C, 80.30; H, 7.16; N, 5.82.
Found: C, 80.59; H, 7.21; N, 5.86.

EXAMPLE 2

4-[Methyl(1,2,3,4-tetrahydro-2-naphthalenyl)amino]-phenol, acetate ester

A.
4-Benzyloxy-N,N-methyl-(1,2,3,4-tetrahydro-2-naphthalenyl)aniline

A mixture of 820 mg (2.49 mmol) of Example 1 Part A compound, 630 mg (7.5 mmol) of powdered sodium bicarbonate and 230 μl (3.7 ml) of iodomethane in 5 ml of dry HMPA was stirred at room temperature for 4 hours. The reaction mixture was added to 50 ml of H$_2$O and extracted with 35 ml of ethyl acetate. The organic extract was separated and washed with an additional 50 ml of H$_2$O. The combined aqueous washes were extracted with 25 ml of chloroform. The organic extracts were combined, dried (Na$_2$SO$_4$) and concentrated in vacuo to give an oil. The crude oil was purified by flash chromatography (12×3.0 cm, 1:19 ether/chloroform) to afford 614 mg (72%) of title compound as a pink solid, m. p. 68°-70°.

Partial 60 MHz $^1$H NMR(CDCl$_3$)
2.78 (s, 3H, —NCH$_3$)
5.02 (s, 2H, —OCH$_2$)
MS(CI): 344 (M+H)$^+$
TLC: Rf(silica gel, 1:9 EtOAc/petroleum ether)=0.61, PMA and UV.

B. 4-Methyl(1,2,3,4-tetrahydro-2-naphthalenyl)amino]-phenol, acetate ester

A mixture of 440 mg (1.28 mmol) of Part A compound and 50 mg of 10% palladium on charcoal catalyst in 10 ml of 1:1 ethyl acetate/methanol was stirred under an atmosphere of hydrogen (balloon) for five hours then filtered through a small column (2×1 cm) of silica gel. The filtrate was concentrated in vacuo to give the phenol as a pale purple foam. To a solution of the crude phenol in 5 ml of CH$_2$Cl$_2$ at 0° was added 200 μl (2.80 mmol) of acetyl chloride and 5 mg of 4-dimethylaminopyridine. The reaction mixture was warmed to room temperature and stirred for two hours. The resulting solution was added to 25 ml of saturated aqueous sodium bicarbonate solution and extracted with 25 ml of ethyl acetate. The organic layer was separated, dried (MgSO$_4$) and concentrated in vacuo to give an orange oil. The crude oil was purified by flash chromatography (10×3.0 cm, 1:3 ether/petroleum ether) to afford 272 mg (72% from Part A compound) of title compound as a white solid, m.p. 93°-94°.

IF(film): 2930, 1755, 1579, 1509, 1367, 1202, 1113, 1012, 745 cm$^{-1}$; 400 MHz $^1$H NMR (CDCl$_3$)
1.93 (m, 1H, —NCHCH$_2$—)
2.05 (m, 1H, —NCHCH$_2$)
2.26 (s, 3H, —COCH$_3$)
2.83 (s, 3H, —NCH$_3$)
2.95 (m, 4H, benzylic methylenes)
4.05 (m, 1H, —NCH—)
6.80 (d, J=9, 2H, benzene aromatics)
6.95 (d, $\bar{J}$=9, 2H, benzene aromatics)
7.09 (m, 4H, tetrahydronaphthalene aromatics)
MS(CI): 296 (M+H)$^+$
TLC: Rf (silica gel, 1:1 ether/petroleum ether)=0.56, PMA and UV, homogeneous.
Microanalysis Calc'd for C$_{19}$H$_{21}$NO$_2$:
Calc'd: C, 77.26; H, 7.17; N, 4.74
Found: C, 77.56; H, 7.10; N, 4.70

EXAMPLE 3
Decanoic acid, 4-[(1,2,3,4-tetrahydro-2-naphthalenyl)methylamino]-phenyl ester

A. 4-[(1,2,3,4-Tetrahydro-2-naphthalenyl)-methylamino]-phenol

A mixture of 1.65 g (4.81 mmol) of Example 2 Part A benzyl ether and 150 mg of 10% palladium on carbon catalyst in 25 ml of 2:3 ethyl acetate/methanol was stirred under an atmosphere of hydrogen (balloon) for 16 hours. The reaction mixture was filtered through a short column of silica gel (EtOAc elution). The filtrate was concentrated in vacuo to give 1.21 g (99%) of crude title compound as a viscous, orange-brown oil.

60 MHz $^1$H NMR (DMSO-d$_6$)
1.90 (m, 2H, cyclohexyl)
2.97–3.10 (m with —NCH$_3$ singlet at 2.70, 7H)
6.80 (m, 4H, aromatic aminophenol protons)
7.13 (s, 4H, tetralin aromatic protons)
TLC: Rf (silica gel, 1:4 EtOAc/petroleum ether)=0.17, PMA and UV.

B. Decanoic acid, 4-[(1,2,3,4-tetrahydro-2-naphthalenyl)methylamino]-phenyl ester To a solution of 414 mg (1.63 mmol) of Part A compound and 219 mg (1.79 mmol, Aldrich) of 4-dimethylaminopyridine in 5 ml of dry CH$_2$Cl$_2$ cooled to 0° was added dropwise a solution of 341 mg (1.79 mmol, Eastman) of decanoyl chloride in 2 ml of CH$_2$Cl$_2$ over five minutes. The reaction mixture was stirred for ten minutes then added to 25 ml of H$_2$O and extracted with 50 ml of ethyl acetate. The organic extract was washed with an additional 25 ml of H$_2$O, dried (Na$_2$SO$_4$) and concentrated in vacuo to give an oil. The crude oil was purified by flash chromatography (silica gel, 15×3.0 cm, 1:9 ether/petroleum ether) to afford 634 mg (96%) of title compound as a colorless oil.

IR(neat): 2926, 2855, 1755, 1511, 1209, 1173, 1143, 1110, 745 cm$^{-1}$.
270 MHz $^1$H NMR(CDCl$_3$)
0.88 (t, 3H, —CH$_2$CH$_3$)
1.28 (m, 12H, —(CH$_2$)$_6$CH$_3$)
1.74 (m, 2H)
1.83–2.10 (m, 2H)
2.51 (t, J=7, 2H, —CO$_2$CH$_2$—)
2.82 (s, 3H, —NCH$_3$)
2.94 (m, 4H, benzylic —CH$_2$—)
4.05 (m, 1H, tetralin methine)
6.80 (d, J=9, 2H, aminophenol aromatics)
6.94 (d, $\bar{J}$=b 9, 2H, aminophenol aromatics)
7.11 (m, 4H, tetralin aromatics)
MS(CI): 408 (M+H)$^+$
TLC: Rf (silica gel, 1:4 ether/petroleum ether)=0.56, PMA (faint) and UV, homogeneous.
Microanalysis Calc'd for C$_{27}$H$_{37}$NO$_2$: C, 79.56; H, 9.15; N, 3.44.
Found: C, 79.75; H, 9.18; N, 3.41.

EXAMPLE 4
2,2-Dimethylpropanoic acid, 4-[(1,2,3,4-tetrahydro-2-naphthalenyl)methylamino]-phenyl ester To a solution of 340 mg (1.34 mmol) of Example 3 Part A compound and 180 mg (1.48 mmol, Aldrich) of 4-dimethylaminopyridine in 5.0 ml of dry CH$_2$Cl$_2$ cooled to 0° was added dropwise a solution of 178 mg (1.48 mmol, Aldrich) of trimethylacetyl chloride in 2 ml of CH$_2$Cl$_2$ over two minutes. The reaction mixture was stirred for 15 minutes then concentrated in vacuo. The residue was partitioned between 25 ml of H$_2$O and 25 ml of ethyl acetate. The organic layer as separated, washed with an additional 25 ml of H$_2$O, dried (Na$_2$SO$_4$) and concentrated in vacuo to give a yellow oil. The crude oil was purified by flash chromatography (15×3.0 cm, 1:9 ether/petroleum ether) to afford 424 mg (94%) of title compound as a colorless oil which solidified upon cooling, m.p. 75°-77°.

IR(KBr): 2965, 1747, 1506, 1479, 1278, 1207, 1173, 1128, 1111, 1093, 745 cm$^{-1}$.
270 MHz $^1$H NMR (CDCl$_3$)
1.34 (s, 9H, —C(CH$_3$)$_3$)
1.92 (dt, $\bar{J}$=3, 9, 1H, C3 proton of tetralin)

2.03 (m, 1H, C3 proton of tetralin)
2 82 (s, 3H, —NCH$_3$)
2.94 (m, 4H, benzylic methylenes of tetralin)
4.01 (m, 1H, tetralin methine)
6.81 (d, J=9, 2H, aminophenol aromatics)
6.92 (d, J=9, 2H, aminophenol aromatics)
7.11 (m, 4H, tetralin aromatics)
MS(CI): 378 (M+H)+
TLC: Rf (silica gel, 1:4 ether/petroleum ether)=0.49, PMA and UV, homogeneous.
Microanalysis Calc'd for C$_{22}$H$_{27}$NO$_2$: C, 78.30; H, 8.06; N, 4.15.
Found: C, 78.50; H, 8.15; N, 4.16.

EXAMPLE 5

4-(2,3-Dihydro-1H-inden-2-yl)amino]phenol

A. 4-Benzyloxy-N-(2,3-dihydro-1H-inden-2-yl)aniline

A solution of 1.00 g (4.2 mmol, Aldrich) of 4-benzyloxyaniline hydrochloride, 555 mg (4.20 mmol, Aldrich) of 2-indanone and 132 mg (2.10 mmol) of sodium cyanoborohydride in 25 ml of MeOH was stirred over 3A molecular sieves at 25° C. for one hour. The mixture was filtered, EtOAc was added and this was washed with saturated NaHCO$_3$, dried (MgSO$_4$) and concentrated in vacuo. Purification via flash chromatography (silica gel, 1:5 EtOAc/petroleum ether) afforded 1.25 g (95%) of title compound as a tan solid: m.p. 72°-75° C.

IR(KBr): 3467, 3396, 3033, 2927, 1512, 1386, 1233, 1126, 1019, 818, 743 cm$^{-1}$;

MHz $^1$H NMR (CDCl$_3$)
δ6 2.82 (d, J=4 Hz, 1H, aliphatic H of indane)
2.88 (d, J=5 Hz, 1H, aliphatic H of indane)
3.30 (d, J=b 5 Hz, 1H, aliphatic H of indane)
3.36 (d, J=6 Hz, 1H, aliphatic H of indane)
3.64 (br s, 1H, —NH—)
4.28 (s, 1H, —NH—CH—)
4.99 (s, 2H, —CH$_2$—C$_6$H$_5$)
6.60 (d, J=8 Hz, 2H, phenol H's)
6.86 (d, J=8 Hz, 2H, phenol H's)
7.19 (m, 4H, aromatic H's of indane)
7.37 (m, 5H, CH$_2$—C$_6$H$_5$)

TLC: Rf (1:2 EtOAc/petroleum ether) =0.66, UV and PMA, homogeneous.

B. 4-[(2,3-Dihydro-1H-inden-2-yl)amino]-phenol

A solution of 1.20 g (3.8 mmol) of Part A compound and 180 mg of 10% palladium on carbon in ml of MeOH and 7 ml of EtOAc was stirred at room temperature under a hydrogen atmosphere (balloon) for 23 hours. The mixture was filtered through a small column of Celite overlaid with sand, eluted with 1:1 EtOAc/MeOH and concentrated in vacuo. Purification via flash chromatography (silica gel, 1:5 EtOAc/petroleum ether) and recrystallization (EtOAC/petroleum ether) afforded 0.57 g (67%) of title compound as white lustrous crystals; m.p. 165°-167° C.

IR(KBr): 3425, 3279, 3042, 2948, 1502, 1446, 1386, 1255, 1228, 1086, 826, 744 cm$^{-1}$;

270 MHz $^1$H NMR (DMSO-d$_6$)
δ 2.71 (d, J=5 Hz, 1H, aliphatic H of indane)
2.77 (d, J=5 Hz, 1H, aliphatic H of indane)
3.23 (m, 2H, aliphatic H's of indane)
4.09 (br m, 1H, NH—CH)
5.10 (s, 1H, —NH or OH)
6.47 (d, J=8 Hz, 2H, phenol H's)
6.56 (d, J=8 Hz, 2H, phenol H's)
7.11 (m, 2H, indane H's)
7.20 (m, 2H, indane H's)
8 36 (s, 1H, —NH or —OH)
MS(CI): 226 (M+H)$^{30}$
TLC: Rf (1:2 EtOAc/petroleum ether)=0.31, UV and PMA, homogeneous.
Microanalysis Calc'd for C$_{15}$H$_{15}$NO:
Calc'd: C, 79.97; H, 6.71; N, 6.22.
Found: C, 79.99; H, 6.78; N, 6.16.

EXAMPLE 6

4-[(1,2,3,4-Tetrahydro-6-methoxy-2-naphthalenyl)amino]phenol

A.

4-Benzyloxy-N(1,2,3,4-tetrahydro-6-methoxy-2-naphthalenyl)aniline

A solution of 977 mg (S.54 mmol, Aldrich) of 6-methoxy-2-tetralone, 1.30 g (5.54 mmol, Aldrich) of 4-benzyloxyaniline hydrochloride and 174 mg (2.77 mmol, Aldrich) of NaBH$_3$CN in 30 ml of MeOH was stirred at 25° C. over 3A molecular sieves for 1.75 hour. The mixture was filtered, saturated NaHCO$_3$ was added and this was extracted with EtOAc. The organic layer was dried (MgSO$_4$) and concentrated in vacuo. Purification via flash chromatography (silica gel, 1:8 EtOAc/petroleum ether) afforded 1.36 g (69%) of title compound as a deep red oil.

IR(Neat): 3393, 3031, 2932, 1611, 1511, 1453, 1382, 1234, 1038, 817, 738, 697 cm$^{-1}$;

270 MHz $^1$H NMR (CDCl$_3$)
1.71 (m, 1H, aliphatic H of tetralin)
2.13 (br m, 1H, aliphatic H of tetralin)
2.58 (dd, J=7, 14, 1H, aliphatic H of tetralin)
2.85 (t, J=6 Hz, 2H, aliphatic H's of tetralin)
3.12 (dd, J=6, 14, 1H, aliphatic H of tetralin)
3 36 (br s, 1H, —NH or CH—)
3.77 (s, 4H, —CH$_3$ and —NHCH— multiplet)
4.99 (s, 2H, —CH$_2$—C$_6$H$_5$)
6.60 (d, J=9, 2H, phenol H's)
6.65 (s, 1H, aromatic H of tetralin)
6.70 (dd, J=2, 9, 1H, aromatic H of tetralin)
6.85 (d, J=9, 2H, phenol H's)
6.98 (d, J=8, 1H, aromatic H of tetralin) 7.25-7.45 (m, 5H, —Ph)

TLC: Rf (silica gel, 1:2 EtOAc/petroleum ether)=0.57, UV and PMA, homogeneous.

B.

4-[(1,2,3,4-Tetrahydro-6-methoxy-2-naphthalenyl)amino]phenol

A solution of 1.33 g (3.71 mmol) of Part A compound and 200 mg of 10% palladium on carbon in 25 ml of 1:4 EtOAc/MeOH was stirred at 25° C. under a hydrogen atmosphere (balloon) for 24 hours. The mixture was filtered through a small column of Celite overlaid with sand, (1:1 EtOAc/MeOH) and the filtrate concentrated in vacuo. Purification via flash chromatography (silica gel, 1:3 EtOAc/petroleum ether) and then recrystallization (EtOAc/petroleum ether) afforded 449 mg (45%) of title compound as a pale purple solid: m.p. 161°-163° C.

IR(KBr): 3279, 2928, 1610, 1500, 1233, 1078, 1040, 835 cm$^{-1}$;

270 MHz $^1$H NMR (CDCl$_3$+DMSO-d$_6$)
1.53 (m, 1H, aliphatic H of tetralin)
2.07 (crude m, 1H, aliphatic H of tetralin)
2.80 (crude t, 2H, aliphatic H's of tetralin)
2.98 (dd, J=6, 14, 1H, aliphatic H of tetralin)

3.48 (br s, 1H, aliphatic H of tetralin)
3.70 (s, 3H, —OCH$_3$)
4.68 (br s, 1H, —NH or —OH)
6.48 (d, J=9, 2H, phenol H's)
6.55 (d, J=9, 2H, phenol H's)
6.65 (d, J=8 with s at 6.63, 2H, aromatics of tetralin)
6.94 (d, J=8, 1H, aromatic H's of tetralin)
8.31 (s, 1H, —NH or —OH)
MS(CI): 270 (M+H)+
TLC: Rf (silica gel, 1:2 EtOAc/petroleum ether)=0.22, UV and PMA, homogeneous.
Microanalysis Calc'd for C$_{17}$H$_{19}$NO$_2$:
Calc'd: C, 75.81; H, 7.11; N, 5.20.
Found: C, 75.53; H, 7.11; N, 5.11.

EXAMPLE 7

4-[(1,2,3,4-Tetrahydro-5,8-dimethoxy-2-naphthalenyl)amino]phenol

A.
6,7-Epoxy-5,6,7,8-tetrahydro-1,4-dimethoxynaphthalene (1) 4a,5,8,8a-Tetrahydro-1,4-naphthaquinone The 1,3-butadiene adduct of p-quinone was prepared as described by van Tamelen, et al., JACS( 91, 7315 (1969). An amount of 500 ml of liquified 1,3-butadiene was added to a mixture of 500 g (4.63M) of p-quinone in 3.5 liters of benzene at 0° C. The five-liter round bottom flask was sealed with a tightly wired rubber stopper and stored in the dark at room temperature for 23 days. The mixture was treated with charcoal, filtered, and evaporated in vacuo. Recrystallization from petroleum ether (12 liters) gave 456.5 g (60.8%) of title solid, m.p. 52°–57° (lit. m.p. 52°–54°).

(2) 5,8-Dihydro-1,4-naphthalene diol

As described in Ber., 62 2345 (1929) an amount of 1 ml of a saturated solution of hydrogen bromide gas in glacial acetic acid was added to a mixture of 104 g (0.642M) of the Part (1) quinone adduct in 174 ml of glacial acetic acid. The solution was stirred for 5 minutes at room temperature before a vigorous exothermic reaction took place (temperature 25°→110° C. over 2 minutes) to give a light tan solid. The solid was collected and washed with hexane to give 100.5 g (0.621M) of title compound, m.p. 208°–211° (lit. m.p. 212°).

(3) 5,8-Dihydro-1,4-dimethoxynaphthalene

A suspension of 63.18 g (0.39 mole) of Part (2) 5,8-dihydro-1,4-naphthalenediol in 300 ml of absolute ethanol was heated briefly until solution was achieved. To this hot stirred solution was added alternately in 5 portions a solution of 40 g (1 mole) of sodium hydroxide in 100 ml of water, and 120 g (89 ml=0.95 mole) of dimethyl sulfate. The heat evolved during the addition caused the solution to reflux. After the addition was complete (approx. 30 minutes), a solution of 10 g of sodium hydroxide in 20 ml of water was added and the mixture was heated overnight at 75°.

The ethanol was removed in vacuo and the aqueous residue was thoroughly extracted with ether. The combined ether extracts were washed with saturated aqueous sodium chloride, dried, and concentrated in vacuo to give 70.40 g (95%) of title compound in the form of tan crystals, m.p. 48°–50°.

(4)
6,7-Epoxy-5,6,7,8-tetrahydro-1,4-dimethoxynaphthalene

To a well-stirred solution of 70.40 g (0.37 mole) of the above olefin in 1.5 liters of methylene chloride at 0°–5° was added 81.5 g (0.40 mole) of 85% m-chloroperbenzoic acid over 5 minutes, and the resulting mixture stirred overnight at room temperature.

The mixture was poured into excess 10% aqueous sodium hydroxide (0°–5°) and the layers separated. The aqueous layer was washed with methylene chloride, the combined organic layers washed with 10% aqueous sodium hydroxide, saturated aqueous sodium chloride, dried, and concentrated in vacuo to give a tan solid. Trituration with isopropyl ether gave 45 g (59%) of tan crystals, m.p. 127°–130°. Recrystallization from isopropyl ether gave title compound in the form of needles, m.p. 130°–131.5°.

B. 1,2,3,4-Tetrahydro-5,8-dimethoxy-2-naphthalenol

To a solution of 0.79 g (3.8 mmol) of Part A compound in 20 ml of dry THF at 0° C. was added mg (7.69 mmol, Aldrich) of lithium aluminum hydride in three portions. The mixture was stirred an additional ten minutes at 0° C., then warmed to 25° C. and stirred for 16 hours. The mixture was cooled to 0° C., H$_2$O was cautiously added, then 1N aqueous HCl was added and this was extracted with EtOAc. The organic extracts were combined, dried (MgSO$_4$) and concentrated in vacuo to yield 790 mg (100%) of title compound as a white solid: m.p. 128°–129° C.

IR(KBr): 3353, 2988, 2939, 2835, 1606, 1481, 1435, 1258, 1097, 1040, 942, 787, 716 cm$^{-1}$;
270 MHz $^1$H NMR (CDCl$_3$)
δ1.75 (m, 1H, aliphatic H of tetralin)
2.01 (m, 1H, aliphatic H of tetralin)
2.60 (dd, J 5, 12, 1H, aliphatic H of tetralin)
2.67 (dd, J=5, 5 1H, aliphatic H of tetralin)
2.90 (ddd, J=5, 5, 12, 1H, aliphatic H of tetralin)
3.05 (dd, J32 5, 12, 1H, aliphatic H of tetralin)
3.77 (s, 7H, —OCH$_3$'s and —OH—)
4.09 (m, 1H, —CH—OH)
6.62 (s, 2H, aromatic)
TLC: Rf (1:1 EtOAc/petroleum ether)=0.25, UV and PMA, homogeneous.

C. 5,8-Dimethoxy-β-tetralone

A solution of 2.89 g (6.81 mmol) of Dess-Martin Periodinane (prepared as described in JOC, 48, 4156 (1983)), and 21 drops of tert-butanol in 10 ml of CH$_2$Cl$_2$ was stirred at 25° C. for 10 minutes then 0.71 g (3.4 mmol) of Part B compound in 16 ml of CH$_2$Cl$_2$ was added and the resulting solution was stirred at 25° C. for 20 hours. The reaction mixture was added to 1N aqueous NaHCO$_3$ and the resulting mixture was extracted twice with Et$_2$O. The organic layers were combined, dried (MgSO$_4$) and concentrated in vacuo. Purification via flash chromatography (silica gel, 1:4 EtOAc/petroleum ether) afforded 270 mg (39%) of title compound as a yellow solid: m.p. 91°–94° C.

IR(KBr): 3406, 2957, 2766, 1709, 1483, 1262, 1081, 798, 714 cm$^{-1}$;
270 MHz $^1$H NMR (CDCl$_3$)
δ2.54 (t, J=7 Hz, 2H, C4 protons)
3.07 (t, J=7 Hz, 2H, C3 protons)
3.50 (s, 2H, C1 protons)
3.77 (s, 3H, —OCH$_3$)

3.80 (s, 3H, —OCH₃)
6.71 (s, 2H, aromatic H's of tetralin)
TLC: Rf (1:1 EtOAc/petroleum ether)=0.58, UV and PMA, homogeneous.

D.
4-Benzyloxy-N-(1,2,3,4-tetrahydro-5,8-dimethoxy-2-naphthalenyl)aniline A solution of 250 mg (1.21 mmol) of Part C compound and 286 mg (1.21 mmol, Aldrich) of 4-benzyloxyaniline hydrochloride in 20 ml of MeOH was stirred over 3A molecular sieves at 25° C. and mg (0.64 mmol) of NaBH₃CN was added. After 2.5 hours, the reaction mixture was filtered, saturated NaHCO₃ was added to the filtrate and this was extracted with EtOAc. The organic layer was dried (MgSO₄) and concentrated in vacuo. Purification via flash chromatography (silica gel, 4 EtOAc/petroleum ether) afforded 350 mg (74%) of title compound as a brown oil.

IR(KBr): 3377, 3062, 3035, 1605, 1511, 1477, 1255, 1100, 797, 743, 713, 698 cm⁻¹;

270 MHz ¹H NMR(CDCl₃)

δ 1.66 (m, 1H, aliphatic H of tetralin)
2.13 (m, 1H, aliphatic H of tetralin)
2.45 (dd, $\bar{J}$=6, 12 Hz, 1H, aliphatic H of tetralin)
2.76 (m, 1H, aliphatic H of tetralin)
2.86 (dt, $\bar{J}$=5, 12 Hz, 1H, aliphatic H of tetralin)
3.17 (dd, $\bar{J}$ 5, 15 Hz, 1H, aliphatic H of tetralin)
3.68 (m, 1H, aliphatic H of tetralin, —CH—NH)
3.75 (s, 3H, —OCH₃)
3.78 (s, 3H, —OCH₃)
4.99 (S, 2H, —CH₂—C₆H₅)
6.60 (d, $\bar{J}$=9 Hz, 2H, phenol H's)
6.63 (s, 2H, aromatic H's of tetralin)
6.85 (d, $\bar{J}$=9 Hz, 2H, phenol H's)
7.37 (m, 5H, —C₆H₅)

TLC: Rf (1:1 EtOAc/petroleum ether)=0.67, UV and PMA, homogeneous.

E.
4-[(1,2,3,4-Tetrahydro-5,8-dimethoxy-2-naphthalenyl)amino]phenol

A solution of 350 mg (0.90 mmol) of Part D compound and 53 mg of 10% palladium on carbon in ml of MeOH and 8 ml of EtOAc was stirred at 25° C. under a hydrogen atmosphere (balloon) for 16 hours. The reaction mixture was filtered through a small column of Celite overlaid with sand, eluted with 1:1 EtOAc/MeOH and concentrated in vacuo. Purification via flash chromatography (silica gel, 1:4 EtOAc/petroleum ether) followed by recrystallization (EtOAc/petroleum ether) afforded 145 mg (54%) of title compound as white crystals: m.p. 188°–189° C.

IR(KBr): 3410, 3274, 2992, 2837, 1603, 1479, 1258, 1113, 1100, 1080, 834, 791, 714 cm⁻¹;

270 MHz ¹H NMR (DMSO-d₆+CDCl₃)

δ1.52 (m, 1H, aliphatic H of tetralin)
2.06 (br s, 1H, aliphatic H of tetralin)
2.33 (dd, $\bar{J}$=6, 12 Hz, 1H, aliphatic H of tetralin)
2.84 (crude dt, 1H, aliphatic H of tetralin)
3.04 (dd, $\bar{J}$=4, 12, 1H, aliphatic H of tetralin)
3.46 (br s, 1H, aliphatic H of tetralin)
3.71 (s, 3H, —OCH )
3.73 (s, 3H, —OCH₃)
4.46 (S, 1H, —NH—)
6.50 (d, J=9 Hz, 2H, phenol H)
6.57 (d, $\bar{J}$=9 Hz, 2H, phenol H)
6.63 (s, 2H, aromatic H's of tetralin)

8.24 (s, 1H, —OH)
MS(CI): 300 (M+H)+
TLC: Rf (1:1 EtOAc/petroleum ether)=0.49, UV and PMA, homogeneous.
Microanalysis Calc'd for C₁₈H₂₁NO₃:
Calc'd: C, 72.22; H, 7.07; N, 4.68.
Found: C, 72.00; H, 7.12; N, 4.62.

EXAMPLE 8
4-[(1,2,3,4-Tetrahydro-6,7-dimethoxy-2-naphthalenyl)amino]phenol

A.
4-Benzyloxy-N-(1,2,3,4-tetrahydro-6,7-dimethoxy-2-naphthalenyl)aniline A solution of 500 mg (2.42 mmol, Aldrich) of 6,7-dimethoxy-2-tetralone and 570 mg (2.42 mmol, Aldrich) of 4-benzyloxyaniline hydrochloride in 20 ml of MeOH was stirred over 3A molecular sieves at 25° C., then 76 mg (1.21 mmol, Aldrich) of NaBH₃CN were added. This mixture was stirred for 3.5 hours, filtered and then saturated NaHCO₃ was added to the filtrate. This solution was extracted with EtOAc twice, the organic layers were combined, dried (MgSO₄) and concentrated in vacuo. Purification via flash chromatography (silica gel, 8, 1:5 then 1:3 EtOAc/petroleum ether) afforded mg (90%) of title compound as a pale pink solid:m.p. 85°–88° C.

270 MHz ¹H NMR(CDCl₃)

δ 1.74 (m, 1H, aliphatic H of dimethoxytetralin)
2.13 (m, 1H, aliphatic H of dimethoxytetralin)
2.58 (dd, $\bar{J}$=6, 12, 1H, aliphatic H of dimethoxytetralin)
2.82 (t, $\bar{J}$=5, 2H, aliphatic H of dimethoxytetralin)
3.10 (dd, $\bar{J}$=4, 12, 1H, aliphatic H of dimethoxytetralin
3.40 (br s, 1H, —NH—)
3.70 (crude m, 1H, —NH—CH—)
3.84 (s, 3H, —OCH₃)
3.86 (s, 3H, —OCH₃)
5.00 (s, 2H, —CH₂—Ph)
6.55 (s, 1H, aromatic H of dimethoxytetralin)
6.60 (s, 1H, aromatic H of dimethoxytetralin)
6.61 (d, J=6, 2H, phenol H's)
6.86 (d, $\bar{J}$=6, 2H, phenol H's) 7.29–7.46 (m, 5H, —C₆H₅)

TLC: Rf (1:1 EtOAc/petroleum ether)=0.66, UV and PMA, homogeneous.

B.
4-[(1,2,3,4-Tetrahydro-6,7-dimethoxy-2-naphthalenyl)amino]phenol

A mixture of 750 mg (1.93 mmol) of Part A compound and 75 mg of 10% palladium on carbon in ml of 1:4 EtOAc/MeOH was stirred at room temperature under a hydrogen atmosphere (balloon) for 2.25 hours. The reaction mixture was filtered through a small column of Celite overlaid with sand, eluted with EtOAc and the filtrate concentrated in vacuo. Purification via flash chromatography (silica gel, 2:5 EtOAc/petroleum ether) and then recrystallization (EtOAc/petroleum ether) afforded 430 mg (74%) of title compound as lustrous pale gold crystals: m.p. 150°–152° C. IR(KBr): 3470, 3009, 2937, 2839, 1610, 1513, 1463, 1357, 1246, 1115, 1017, 973, 826, 787 cm⁻¹;

270 MHz ¹H NMR (CDCl₃)

δ 1.74 (m, 1H, C3 proton of tetralin)
2.09 (crude m, 1H, C3 proton of tetralin)

2.59 (dd, J=8, 16, 1H, C1 proton of tetralin)
2.81 (t, J=6, 2H, C4 protons of tetralin)
3.10 (dd, J=4, 16, 1H, C1 proton of tetralin)
3.73 (m, 2H, —NH and —NHCH—)
3.83 (s, 3H, —OCH$_3$)
3.84 (s, 3H, —OCH$_3$)
6.56 (s, 1H, C5 or C8 proton of tetralin)
6.57 (d, J=8, 2H, phenol H's)
6.60 (s, 1H, C5 or C8 proton of tetralin)
6.70 (d, J=8, 2H, phenol H's)
MS(CI): 300 (M+H)
TLC: Rf (1:1 EtOAc/petroleum ether)=0.25, UV and PMA, homogeneous.
Microanalysis Calc'd for C$_{18}$H$_{21}$NO$_3$:
Calc'd: C, 72.22; H, 7.07; N, 4.68.
Found: C, 72.00; H, 7.12; N, 4.62.

EXAMPLE 9

4-[Methyl(1,2,3,4-tetrahydro-6-methoxy-2-naphthalenyl)aminophenol, acetate ester A.
4-Benzyloxy-N,N-(1,2,3,4-tetrahydro-6-methoxy-2-naphthalenyl)methyl aniline A solution of 1.27 g (3.53 mmol) of Example 6 Part A compound, 890 mg (10.6 mmol, 3 eq.) of powdered sodium bicarbonate and 440 μl (7.06 mmol, 2 eq.) of methyl iodide in 15 ml of dry hexamethyl phosphoric triamide (HMPA) was stirred at 25° C. for 1.75 hours, then H$_2$O was added. This mixture was extracted with EtOAc twice, the organic layers were combined, washed with H$_2$O, dried (MgSO$_4$) and concentrated in vacuo. Purification via flash chromatography (silica gel, 1:12 EtOAc/petroleum ether) afforded 0.99 g (76%) of title compound as a pale pink solid: m.p. 107°–110° C.
IR(KBr): 3437, 2915, 1605, 1513, 1466, 1286, 1234, 1185, 1106, 1019, 965, 814, 759, 736, 698 cm$^{-1}$.
270 MHz $^1$H NMR (CDCl$_3$)
1.65 (dt, J=7, 9, 1H, C3 proton of tetralin)
2 03 (m, 1H, C3 proton of methoxytetralin)
2.74–2.91 (br m, 7H, including 4 protons of methoxytetralin)
2.78 (s, 3H, Me—N—)
3.76 (s, 3H, —OCH$_3$)
3.77 (m, 1H, Me—N—CH—)
5.00 (s, 2H, —CH$_2$—C$_6$H$_5$)
6.63 (s, 1H, C5 aromatic proton of methoxytetralin)
6.68 (s, J=10, 1H, aromatic proton of methoxytetralin)
6.83 (d, J=9, 2H, phenol H's)
6.90 (d, J=9, 2H, phenol H's)
6.97 (d, J=8, 1H, aromatic proton of methoxytetralin)
7.29–7.43 (m, 5H, —C$_6$H$_5$)
TLC: Rf (1:2 EtOAc/petroleum ether)=0.51, UV and PMA, homogeneous.

B.
4-[Methyl(1,2,3,4-tetrahydro-6-methoxy-2-naphthalenyl)amino]phenol

A solution of 0.87 g (2.33 mmol) of Part A compound and 130 mg of 10% palladium on carbon in 17 ml of EtOAc and 38 ml of MeOH was stirred at 25° C. under a hydrogen atmosphere (balloon) for 2.5 hours. The reaction mixture was filtered through a small column of Celite overlaid with sand, eluted with EtOAc, and the filtrate was concentrated in vacuo. Purification was accomplished by flash chromatography (2:5 EtOAc/petroleum ether) then recrystallization (EtOAc/petroleum ether) to yield 362 mg of title compound as a pink foam.
IR(KBr): 3385, 2936, 1611, 1512, 1454, 1441, 1265, 1236, 1037, 964, 816, 734 cm$^{-1}$;
270 MHz $^1$H NMR (DMSO-d$_6$)
1.70 (m, 1H, C$_3$ proton of methoxytetralin)
1.86 (m, 1H, C$_3$ proton of methoxytetralin)
2.65 (s, 3H, —N—CH$_3$)
2.67 (m, 2H, C$_1$ or C$_4$ protons of methoxytetralin)
2.83 (m, 2H, C$_1$ or C$_4$ protons of methoxytetralin)
3.69 (m, 1H, for CH$_3$N—CH and s, 3H, —OCH$_3$)
6.63 (d, J=9, 2H, phenol H's)
6.64 (s, 1H, C$_5$ of methoxytetralin)
6.67 (d, 1H, aromatic H of methoxytetralin)
6.70 (d, J=9, 2H, phenol H's)
6.95 (d, J=8, 1H, aromatic H of methoxytetralin)
8.64 (s, 1H, —OH)
MS(CI): 284 (M+H)$^+$
TLC: Rf (1:2 EtOAc/petroleum ether)=0.19, UV and PMA, homogeneous.

C.
4-[Methyl(1,2,3,4-tetrahydro-6-methoxy-2-naphthalenyl)amino]phenol

A solution of 0.40 g (1.4 mmol) of Part B compound, 165 μl (2.32 mmol) of acetylchloride and 900 μl (7.05 mmol) of dimethylaniline in 5 ml of dry CH$_2$Cl$_2$ was stirred at 25° C. for 18 hours. To the reaction solution was added 1N aqueous HCl and the resulting mixture was extracted twice with EtOAc. The organic layers were combined, dried (MgSO$_4$) and concentrated in vacuo. Purification via flash chromatography (silica gel, 1:10 EtOAc/petroleum ether) afforded a clear oil, which upon addition of Et$_2$O yielded 145 mg (35%) of title compound as a white solid: m.p. 79°–82° C.
IR(KBr): 3425, 2948, 1748, 1607, 1513, 1366, 1268, 1228, 1200, 1155, 1039, 826 cm$^{-1}$;
270 MHz $^1$H NMR (CDCl$_3$)
1.94 (br m, 2H, C$_3$ proton of tetralin)
2.25 (s, 3H, —OCOCH$_3$)
2.82 (s, 3H, —NCH$_3$)
2.88 (m, 4H, benzylic methylenes of tetralin)
3.77 (s, 3H, OCH$_3$)
4.00 (br s, 1H, tetralin methine)
6.65 (s, 1H, C$_5$ aromatic H of tetralin)
6.70 (d, J=8 Hz, 1H, C$_7$ aromatic H of tetralin)
6.79 (d, J=9 Hz, 2H, phenol H's)
6.94 (d, J=9 Hz, 2H, phenol H's)
6.98 (d, J=8 Hz, 1H, C$_8$ aromatic H of tetralin)
MS(CI): 326 (M+H)$^+$
TLC: Rf (silica gel, 1:3 EtOAc/petroleum ether)=0.33 UV and PMA, homogeneous.
Microanalysis Calc'd for C$_{20}$H$_{23}$NO$_3$:
Calc'd: C, 73.83; H, 7.12; N, 4.30.
Found: C, 73.65; H, 7.06; N, 4.24.

EXAMPLE 10

5,6,7,8-Tetrahydro-6-[(4-hydroxyphenyl)amino]-2-naphthalenol

A solution of 250 mg (0.93 mmol) of Example 6 compound in 5 ml of dry CH$_2$Cl$_2$ was cooled to −78° C. and 2.80 ml (2.80 mmol, 1M in CH C$_{12}$, Aldrich) of BBr$_3$ was added dropwise. The solution was warmed to room temperature. After three hours, saturated NaHCO$_3$ was slowly added (until gas evolution subsided) and the solution was extracted twice with EtOAc. The organic layers were combined, washed with H₂O, dried (MgSO₄) and concentrated in vacuo. Purification via recrystallization (EtOAc/petroleum ether) afforded 157 mg (66%) of title compound as a brown solid: m.p. 193°–195° C.

IR(KBr) 3357, 3025, 2931, 1606, 1511, 1449, 1361, 1228, 1107, 1073, 1047, 834 cm⁻¹;

270 MHz ¹H NMR (DMSO-d₆)

δ1 47 (m, 1H, aliphatic H of tetralin)
2.03 (m, 1H, aliphatic H of tetralin)
2.73 (crude t, 2H, aliphatic H's of tetralin)
2.90 (dd, J=4, 9, 1H, aliphatic H of tetralin)
3.44 (m, 1H, tetralin methine)
4.76 (br s, 1H, —NH—)
6.51 (m, 6H, 4 H's of phenol, 2 aromatic H's of tetralin)
6.83 (d, J=8 Hz, 1H, aromatic H of tetralin)
8.34 (s, 1H, OH)
8.96 (s, 1H, OH)
MS(CI): 256 (M+H)⁺
TLC: Rf (1:1 EtOAc/petroleum ether)=0.25, UV and PMA, homogeneous.

Microanalysis Calc'd for C₁₆H₁₇NO₂:
Calc'd: C, 75.27; H, 6.71; N, 5.49.
Found: C, 74.93; H, 6.82; N, 5.29.

EXAMPLE 11

4-[(2,3-Dihydro-5-methoxy-1H-inden-2-yl)amino]-phenol

A. 5-Methoxy-1-indanone tosylhydrazone

A mixture of 5.00 g (31 mmol, Aldrich) of 5-methoxy-1-indanone and 6.33 g (34.0 mmol, Aldrich) of p-toluenesulfonhydrazide in 50 ml EtOH was heated on a steam bath until homogeneous. The solution was cooled and the solid which formed was filtered to yield 10.05 g (99%) of title compound as cream colored crystals: m.p. 195°–196° C.

IR(KBr): 3432, 3208, 1604, 1491, 1403, 1346, 1329, 1256, 1166, 1069 cm⁻¹

60 MHz ¹H NMR (CDCl₃)

2.40 (s, 3H, —NHC₆H₄CH₃)
2.68 (m, 2H, aliphatic H's of indane)
3.00 (m, 2H, aliphatic H's of indane)
3.80 (s, 3H, —OCH₃)
6.79 (d, J=7 Hz, 2H, aromatic H's of indane)
7.30 (d, J=7 Hz, 2H, H's of toluene)
7.59 (m, 2H, —NH, aromatic H of indane)
7.92 (d, J=8 Hz, 2H, H's of toluene)
TLC: Rf (1:1 EtOAc/petroleum ether)=0.40 UV only.

B. 6-Methoxyindene

A solution of 10.0 g (30.3 mmol) of Part A compound in 300 ml of ether was stirred at 25° C. and 53.5 ml (90.9 mmol, 1.7M in ether) of methyllithium was added dropwise via an additionl funnel. After 2.5 hours, water was slowly added to quench the excess MeLi, then an additional 200 ml of H₂O was added and this was extracted twice with 150 ml portions of ether. The organic layers were combined, dried (MgSO₄) and concentrated in vacuo. Purification via flash chromatography (silica gel, 1:15 EtOAc/petroleum ether) afforded 3.32 mg (75%) of title compound as a yellow oil.

IR(film): 3452, 2957, 2926, 2855, 1728, 1606, 1490, 1463, 1273, 1123, 1073, 1036 cm⁻¹;

60 MHz ¹H NMR (CDCl₃)

3.33 (s, 2H, aliphatic H's of indene)
3.73 (s, 3H, —OCH )
6.40 (dd, J=2, 6 Hz, olefin H)
6.82 (m, 3H, 1H of olefin 2 aromatic H's of indene)
7.26 (dd, J=2, 8 Hz, 1H, aromatic H of indene)
TLC: Rf (1:4 EtOAc/petroleum ether)=0.59, UV and PMA.

C. 5-Methoxy-2-indanol

To a solution of 3.30 g (22.6 mmol) of Part B compound in 30 ml of hexane was added dropwise at 0° C. 2.6 ml (26.0 mmol, Aldrich) of borane methyl sulfide. The reaction mixture was warmed to 25° C., stirred for 18 hours, then cooled to 0° C. Added slowly to the resulting solution was 10 ml of EtOH, followed by the slow addition of 7 ml (20.3 mmol) of 3N NaOH and finally, the slow addition of 3 ml (30 mmol) of 30% H₂O₂. The resulting mixture was refluxed for one hour, cooled and brine was added. This mixture was extracted with EtOAc twice, the organic layers were combined, dried (MgSO₄) and concentrated in vacuo. Purification via flash chromatography (silica gel, 1:4 EtOAc/petroleum ether) afforded 2.96 g (80%) of title compound as a white solid: m.p. 67°–69° C.

IR(KBr): 3273, 2949, 2836, 1606, 1588, 1490, 1464, 1452, 1425, 1338, 1251, 1205, 1193, 1143, 1085, 1035, 953, 806 cm⁻¹;

270 MHz ¹H NMR (CDCl₃)

1.95 (s, 1H, —OH)
2.82 (dt, J=3, 14 Hz, 2H, aliphatic H's of indanol)
3.14 (ddd, J=7, 9, 15 Hz, 2H, aliphatic H's of indanol)
3.76 (s, 3H, —OCH₃)
4.65 (s, 1H, —HO—C—H)
6.71 (dd, J=2, 8 Hz, 1H, aromatic H of indanol)
6.78 (s, 1H, aromatic H of indanol)
7.11 (d, J=8 Hz, 1H, aromatic H of indanol)
TLC: Rf (1:3 EtOAc/petroleum ether)=0.11, UV and PMA.

D. 5-Methoxy-2-indanone

A solution of 3.77 g (8.89 mmol, Aldrich) of Dess-Martin Periodinane and 32 drops of t-butanol in 20 ml of dry CH₂Cl₂ was stirred at 25° C. for five minutes, then a solution of 729 mg (4.44 mmol) of Part C compound in 20 ml of dry CH₂Cl₂ was added. This solution was stirred at 25° C. for one hour and concentrated in vacuo. The residue was purified via flash chromatography (silica gel, 1:6 EtOAc/petroleum ether) and recrystallization (ether/petroleum ether) to afford 540 mg (75%) of title compound as white crystals: m.p. 74°–78° C.

IR(KBr): 3469, 3014, 2969, 2940, 2899, 1744, 1703, 1608, 1583, 1493, 1457, 1389, 1281, 1232, 1191, 1178, 1141, 1077, 1029, 821 cm⁻¹;

60 MHz ¹H NMR (CDCl₃)

3.52 (s, 4H, aliphatic H's of indanone)
3.84 (s, 3H, —OCH₃)
6.92 (m, 2H, aromatic H's of indanone)
7.24 (crude d, aromatic H's of indanone)
TLC: Rf (1:3 EtOAc/petroleum ether)=0.32, UV and

E. 4-Benzyloxy-N-(2,3-dihydro-5-methoxy-1H-inden-2-yl)aniline

A solution of 546 mg (3.37 mmol) of Part D compound and 794 mg (3.37 mmol, Aldrich) of -benzyloxyaniline hydrochloride in 30 ml of MeOH was stirred over 3A molecular sieves and 106 mg (1.69 mmol) of NaBH₃CN was added. This was stirred for two hours, filtered and the filtrate was added to saturated NaHCO$_3$. The resulting solution was extracted with EtOAc. The organic layer was dried (MgSO$_4$), concentrated in vacuo and the crude material purified via flash chromatography (silica gel, 1:4 EtOAc/petroleum ether) to afford 1.04 g (90%) of title compound as a yellow solid: m.p. 55°–57° C.

IR(Film): 3392, 3030, 2938, 1610, 1510, 1233, 1127, 1028, 818, 740, 697 cm$^{-1}$;

270 MHz $^1$H NMR (CDCl )
2.79 (dt, J=2, 4Hz, 2H, aliphatic H's of indane)
3.27 (ddd, J=2, 2, 4 Hz, 2H, aliphatic H's of indane)
3.77 (s, 3H, —OCH$_3$)
4.27 (m, 1H, methine)
4.98 (s, 2H, —CH$_2$—C$_6$H$_5$)
6.58 (d, J=9 Hz, 2H, phenol H's )
6.72 (d, J=8 Hz, 1H, C$_4$ of indane)
6.77 (s, 1H, C$_6$ of indane)
6.84 (d, J=9 Hz, 2H, phenol H's ) 7.10 (d, J=8 Hz, 1H, C$_7$ C$_7$ of indane) 7.29–7.40 (m, 5H, —C$_6$H$_5$)

TLC: Rf (1:1 EtOAc/petroleum ether) =0.70, UV and PMA, homogeneous.

F.
4-[(2,3-Dihydro-5-methoxy-1H-inden-2-yl)amino]phenol

A solution of 0.93 g (2.70 mmol) of Part E compound and 140 mg of 10% palladium on carbon in ml of MeOH and 5 ml of EtOAc was stirred at 25° C. under a hydrogen atmosphere (balloon) for two hours. The reaction was filtered through a small column of Celite overlaid with sand, eluted with EtOAc, and the filtrate was concentrated in vacuo. Purification was accomplished via recrystallization (EtOAc/petroleum ether) to yield mg (86%) of title compound as a pale brown solid: m.p. 144°–146° C.

IR(KBr): 3277, 2940, 2833, 1618, 1584, 1493, 1435, 1384, 1325, 1251, 1111, 1033, 828, 806 cm$^{-1}$;

270 MHz $^1$H NMR (CDCl$_3$+DMSO-d$_6$)
2.79 (overlapping dd, 2H, aliphatic H's of indane)
3.26 (overlapping dd, 2H, aliphatic H's of indane)
3.57 (br s, 1H —NH—)
3.77 (s, 3H, —OCH$_3$)
4.25 (m, 1H, methine)
6.53 (d, J=9 Hz, 2H, phenol aromatics)
6.73 (m, 4H, phenol aromatics and indane aromatics)
7.10 (d, J=9 Hz, 1H, aromatic H of indane)
7.56 (br s, 1H, —OH)
MS(CI) 256 (M+H)+

TLC: Rf (silica gel, 1:1 EtOAc/petroleum ether)=0.55, UV and PMA, homogeneous.

Microanalysis Calc'd for C$_{16}$H$_{17}$NO$_2$:
Calc'd: C, 75.27; H, 6.71; N, 5.49.
Found: C, 74.88; H, 6.83; N, 5.39.

EXAMPLE 12

-[(2,3-Dihydro-1H-inden-2-yl)methylamino]phenol, acetate ester

A. 4-Benzyloxy-N-(2,3-dihydro-1H-inden-2-yl)aniline

A solution of 2.00 g (15.1 mmol, Aldrich) of 2-indanone and 3.57 g (15.1 mmol, Aldrich) of 4-benzyloxyaniline hydrochloride in 30 ml of methanol was stirred over 3Å molecular sieves at 25° C. and 476 mg (7.57 mmol, Aldrich) of NaBH$_3$CN was added in four portions. The resulting yellow solution was stirred at 25° C. for approximately two hours, filtered and the filtrate added to saturated NaHCO$_3$. This was extracted with EtOAc twice, the organic layers were combined, dried (MgSO$_4$) and concentrated in vacuo. Purification via flash chromatography (silica gel, 1:7 EtOAc/petroleum ether) afforded 3.02 g (64%) of title compound as an off-white solid: m.p. 74°–76° C.

MHz $^1$H NMR (CDCl$_3$)
δ 2.86 (dd, J=4, 8, 2H, C$_1$ or C$_3$ H's of indane)
3.30 (dd, J=4, 8, 2H, C$_1$or C$_3$ H's of indane)
3.61 (br s, 1H, —NH—)
4 30 (m, 1H, —NH—)
5.00 (s, 2H, —C$_6$H$_5$)
6.58 (d, J=7, 2H, aromatic H's of phenol)
6.85 (d, J=7, 2H, aromatic H's of phenol)
7.10–7.24 (m, 4H, aromatic H's of indane)
7.27–7.46 (m, 5H, —C$_6$H$_5$)

TLC: Rf (1:5 EtOAc/petroleum ether) - 0.32, UV and PMA, homogeneous.

B.
4-Benzyloxy-N-methyl-N-(2,3-dihydro-1H-inden-2-yl)aniline

A solution of 2.90 g (9.2 mmol) of Part A compound, 2.32 g (27.6 mmol) of NaHCO$_3$ and 1.15 ml (18.4 mmol) of MeI in 20 ml of dry HMPA was stirred at 25° C. for 2.25 hours. Water was added, and the resulting mixture was extracted with EtOAc twice. The organic layers were combined and washed several times with H$_2$O in order to remove the residual HMPA. The organic layer was dried (MgSO$_4$) and concentrated in vacuo. Purification via flash chromatography (silica gel, 1:10 EtOAc/petroleum ether) afforded 1.86 g (61%) of title compound as a white solid, m.p. 79°–80° C.

IR(KBr): 3015, 3002, 2933, 2915, 2877, 1509, 1453, 1271, 1239, 1217, 1159, 1023, 825, 751, 741, 703 cm$^{-1}$;

270MHz $^1$H NMR (CDCl$_3$)
δ 2.67 (s, 3H, —N—CH$_3$)
2.99 (dd, J=7, 7, 2H, C$_1$or C$_3$ of indane)
3.11 (dd, J=7, 7, 2H, C$_1$ or C$_3$ of indane)
4.48 (dt, J=7, 7, 1H, —NH—CH)
5.00 (s, 2H, —CH$_2$C$_6$H$_6$)
6.90 (s, 4H, aromatic H's of indane)
7.15 (m, 4H, aromatic H's of phenol)
7.20–7.43 (br m, 5H C$_6$H$_5$)

TLC: Rf (1:5 EtOAc/petroleum ether)=0.33, UV and PMA, homogeneous.

C. 4-[(2,3-Dihydro-1H-inden-2-yl)methyl-amino]phenol

A solution of 1.72 g (5.23 mmol) of Part B compound and 0.26 g of 10% palladium on carbon in ml of EtOAc and 32 ml of MeOH was stirred at 25° C. under a hydrogen atmosphere (balloon) for 4.25 hours. The reaction mixture was filtered through a small column of Celite overlaid with sand, eluted with EtOAc, and the filtrate was concentrated in vacuo to yield 1.27 g (100%) of title compound as an off-white solid: m.p. 106°–109° C.

IR(KBr): 2925, 1513, 1481, 1453, 1443, 1273, 1257, 1238, 1205, 970, 828, 817, 758 cm$^{-1}$;

60 MHz $^1$H NMR (CDCl$_3$)
δ 2.53 (s, 3H, —N—CH$_3$)
2.88 (dd, J=6, 6, 2H, C$_1$ or C$_3$ of indane)
3.02 (dd, J=6, 6, 2H, C$_1$or C$_3$ of indane)
4.36 (crude dt, J=4, 6, 1H, CH$_3$——CH)
6.65 (d, J=9, 2H, phenol H's )
6.81 (d, J=9, 2H, phenol H's )
7.14 (m, 4H, aromatic H's of indane)
8.74 (s, 1H, —OH)

TLC: Rf (1:3 EtOAc/petroleum ether)=0.22, UV and PMA, homogeneous.

D.
4-[(2,3-Dihydro-1H-inden-2-yl)methyl-amino]phenol, acetate ester

A solution of 500 mg (2.10 mmol) of Part C compound and 282 mg (2.31 mmol, Aldrich) of dimethylaminopyridine in 5 ml of dry $CH_2Cl_2$ was stirred at 0° C., then 164 μl (2.31 mmol) of acetyl chloride in 5 ml of dry $CH_2Cl_2$ was added dropwise. The reaction mixture was stirred for 45 minutes at 25° C. and concentrated in vacuo. Water was added to the residue and this was extracted with EtOAc twice, dried ($MgSO_4$) and concentrated in vacuo. Recrystallization (EtOAc/petroleum ether) of the crude material afforded 470 mg (80%) of title compound as lustrous white crystals: m.p. 88°–90° C.

IR(KBr): 3470, 3434, 2941, 2923, 1754, 1603, 1509, 1371, 1298, 1225, 1160, 935, 757 cm$^{-1}$
270 MHz $^1$H NMR ($CDCl_3$)
δ 2.26 (s, 3H, —$OCOCH_3$)
2.73 (s, 3H, —N—$CH_3$)
3.03 (dd, J=6 7, 2H, $C_1$ or $C_3$ H's of indane)
3.17 (dd, $\bar{J}$=7, 8, 2H, $C_1$ or $C_3$ H's of indane)
4.69 (dt, $\bar{J}$=4, 6, 1H, $CH_3N$—CH)
6.84 (d, $\bar{J}$=9, 2H, phenol H's )
6.96 (d, $\bar{J}$=9, 2H, phenol H's)
7.23–7.14 (m, 4H, aromatic H's of indane)
MS(CI): 282 (M+H)$^+$
TLC: Rf (silica gel, 1:3 EtOAc/petroleum ether)=0.50, UV and PMA, homogeneous.
Microanalysis Calc'd for $C_{18}H_{19}NO_2$:
Calc'd: C, 76.84; H, 6.80; N, 4.98.
Found: C, 76.64; H, 6.94; N, 4.86.

Example 13
4-[(2,3-Dihydro-1H-inden-2-yl)methylamino]phenol, decanoate ester A solution of 600 mg (2.51 mmol) of Example 12 Part C compound and 337 mg (2.76 mmol) of 4-dimethylaminopyridine in 5 ml of dry $CH_2Cl_2$ was cooled to 0° C. and a solution of 590 μl (2.84 mmol) of decanoyl chloride in 5 ml of dry $CH_2Cl_2$ was added dropwise. The reaction mixture was stirred for 45 minutes at 25° C. and concentrated in vacuo. The residue was partitioned between ethyl acetate and water. The organic layer was separated, dried ($MgSO_4$) and concentrated in vacuo to give a solid. Recrystallization (EtOAc/petroleum ether) of the crude material afforded 660 mg (67%) of title compound as lustrous white crystals: m.p. 48°–49° C.

IR(KBr): 3450, 2922, 2851, 1757, 1748, 1511, 1469, 1328, 1291, 1211, 1198, 1175, 1143, 829, 753 cm$^{-1}$;
270 MHz $^1$H NMR ($CDCl_3$)
δ 0.87 (t, 3H, —$(CH_2)_8CH_3$0
1.28 (br m, 12H —$(CH_2)_6CH_3$)
1.74 (dt, J=6, 7, 2H, —$CH_2$—n—$C_7H_{15}$)
2.52 (t, $\bar{J}$=7, 2H, $CH_2$—n—$C_8H_{17}$)
2.73 (s, $\bar{3}$H, —$NCH_3$) 3.03 (dd, J=8, 16 Hz, 2H, $C_1$ or $C_3$ H's of indane)
3.17 (dd, J=8, 16 Hz, 2H, $C_1$ or $C_3$ H's of indane)
4.69 (dt, $\bar{J}$=4, 6 Hz, 1H, MeN—CH)
6 B4 (d, $\bar{J}$=9 Hz, 2H, phenol H's )
6.95 (d, $\bar{J}$=9 Hz, 2H, phenol H's )
7.14–7.23 (m, 4H, aromatic H's of indane)
MS(CI): 394 (M+H)$^+$
TLC: Rf (silica gel, 1:3 EtOAc/petroleum ether)=0.70, UV and PMA, homogeneous.
Microanalysis Calc's for $C_{26}H_{35}NO_2$:
Calc'd: C, 79.35; H, 8.96; N, 3.56.
Found: C, 79.27; H, 9.01; N, 3.60.

EXAMPLES 14 to 31

Following the procedures as outlined in the Specification and the working Examples, the following additional compounds in accordance with the present invention may be prepared.

| Ex. No. | R$^4$ | R$^1$ (position) | R$^3$ | $(CH_2)_n$ | $(R^2)_m$ (position) |
|---|---|---|---|---|---|
| 14. | H | H | $C_2H_5$ | $CH_2$ | $C_2H_5O$ (6) |
| 15. | $CH_3$ | $C_2H_5O$ (3) | H | $(CH_2)_2$ | $(C_3H_7O)_2$ (6, 7) |
| 16. | $CH_3C(O)$— | $C_6H_5$ (2) | $C_3H_7C(O)$— | $(CH_2)_3$ | OH (6) |
| 17. | H | OH (3) | $C_6H_5C(O)$— | $CH_2$ | $CH_3O$— (7) |
| 18. | $C_2H_5$ | $(CH_2)_3O$ (2) | H | $(CH_2)_2$ | $C_2H_5O$ (6) |
| 19. | $C_2H_5C(O)$— | $C_2H_5S$ (3) | H | —$CH_2$—$CH(CH_3)$— | $C_3H_7O$ (8) |

-continued

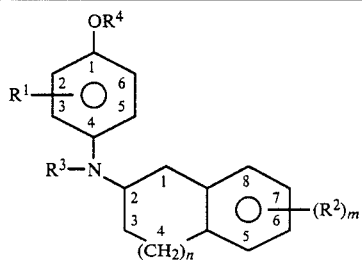

| Ex. No. | $R^4$ | $R^1$ (position) | $R^3$ | $(CH_2)_n$ | $(R^2)_m$ (position) |
|---|---|---|---|---|---|
| 20. | H | $CH_3O$ (6) | $C_3H_7$ | $-CH_2-C(CH_3)_2-$ | $CH_3O$ (7) |
| 21. | $C_3H_7$ | H | $C_4H_9CO-$ | $-CH_2-$ | $C_2H_5O$ (3) |
| 22. | $C_3H_7CO-$ | $C_2H_5CO$ (3) | $C_6H_5CO-$ | $-(CH_2)_2-$ | $C_4H_9O$ (4) |
| 23. | H | $C_6H_5CO$ (2) | $C_6H_{13}$ | $-(CH_2)_3-$ | $C_5H_{11}O$ (5) |
| 24. | $C_4H_9$ | Cl (5) | $C_5H_{11}$ | $-CH(CH_3)-$ | $C_2H_5O$ (6) |
| 25. | $C_4H_9CO-$ | $CO_2H$ (2) | $C_4H_9CO-$ | $-CH_2-$ | $(OH)_2$ (6, 7) |
| 26. | H | $CH_3OC(=O)$ (3) | H | $-CH_2-$ | $CH_3O$ (6) |
| 27. | $C_5H_{11}$ | $NH_2C(=O)-$ (6) | H | $-CH_2-$ | $C_2H_5O$ (7) |
| 28. | $C_5H_{11}C(=O)-$ | $CNH_2$ (3) | $CH_3$ | $-CH_2-$ | H |
| 29. | H | $CNH_2$ (5) | H | $-CH_2-$ | H |
| 30. | $C_6H_{13}$ | H | $C_2H_5$ | $-CH_2-$ | $C_3H_7O$ (5) |
| 31. | $C_6H_{13}C(=O)-$ | H | H | $-(CH_2)_2-$ | $C_5H_{11}O$ (6) |

What is claimed is:

1. A compound having the structure

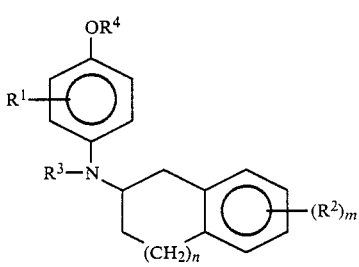

wherein m is 0 or 2; n is 1; $R^1$ and $R^2$ may be the same or different and are H, hydroxy, or alkoxy, $R^3$ is H, lower alkyl, alkanoyl or aroyl; and $R^4$ is H, lower alkyl or alkanoyl, and including acid-addition salts thereof.

2. The compound as defined in claim wherein $R^4$ is H.

3. The compound as defined in claim 2 wherein $R^1$ is H.

4. The compound as defined in claim 1 having the name 4-[(1,2,3,4-tetrahydro-2-naphthalenyl)amino]-phenol.

5. The compound as defined in claim 1 having the name 4-[(1,2,3,4-tetrahydro-5,8-dimethoxy-2-naphtalenyl)amino]phenol.

6. The compound as defined in claim 1 having the name 4-[(1,2,3,4-tetrahydro-6,7-dimethoxy-2-naphthalenyl)amino]phenol.

7. The compound as defined in claim 1 having the name decanoic acid, 4-[(1,2,3,4-tetrahydro-2-naphthalenyl)methylamino]phenyl ester.

8. A compound having the structure

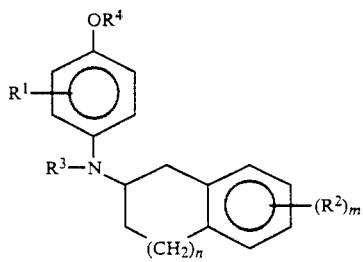

wherein m is 1 or 2; n is 0; $R^1$ is H, hydroxy, or alkoxy and $R^2$ is hydroxy, or alkoxy; $R^3$ is H, lower alkyl, alkanoyl or aroyl; and R4 is H, lower alkyl or alkanoyl, and including acid-addition salts thereof.

9. The compound as defined in claim 8 having the name 4-[(2,3-dihydro-5-methoxy-1H-iden-2-yl)amino]-phenol.

10. A method of inhibiting leukotriene biosynthesis to treat inflammation or psoriasis, which comprises administering to the circulatory system of a mammalian host an effective amount of a compound having the structure

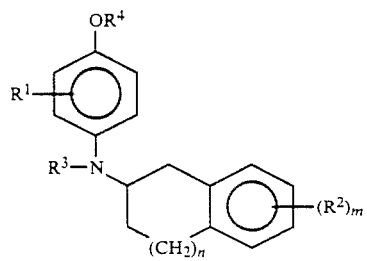

wherein m is 0, 1, or 2; n is 0, ', 2 or 3; $R^1$ is $R^2$ may be the same or different and are H, hydroxy, or alkoxy; $R^3$ is H, lower alkyl, alkanoyl or aroyl; and R4 is H, lower alkyl or alkanoyl or a pharmaceutically acceptable salt thereof.

11. The method as defined in claim 10 wherein said compound is administered in an amount within the range of from about 1 to about 100 mg/kg.

12. The compound having the name the acetate ester of 4-[methyl(1,2,3,4-tetrahydro-2-naphthalenyl)amino]-phenol.

13. The compound having the name 2,2-dimethylpropanoic acid, 4-[(1,2,3,4-tetrahydro-2naphthalenyl)-methylamino]phenyl ester.

14. The compound having the name the acetate ester of 4-[methyl(1,2,3,4-tetrahydro-6-methoxy-2-naphthalenyl)amino]phenol.

15. A composition for inhibiting allergic conditions mediated by leukotrienes in a mammalian species, comprising an effective amount of a compound having the structure

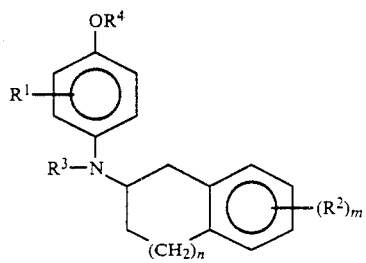

wherein m is 0, 1 or 2; n is 1; $R^1$ and $R^2$ may be the same or different and are H, hydroxy, or alkoxy; $R^3$ is H, lower alkyl, alkanoyl or aroyl; and $R^4$ is alkanoyl, or a pharmaceutically acceptable salt thereof, and a pharmaceutically acceptable carrier therefor.

16. A method for treating asthma in a mammalian species in need of such treatment, which comprises administering to a mammalian host an effective amount of a compound having the structure

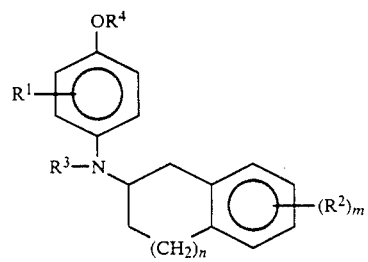

wherein m is 0, 1 or 2; n is 0, 1, 2 or 3; $R_2$ and $R^2$ may be the same or different and are H, hydroxy, or alkoxy; $R^3$ is H, lower alkyl, alkanoyl or aroyl; and $R^4$ is H, lower alkyl or alkanoyl or a pharmaceutically acceptable salt thereof.

17. A compound having the structure

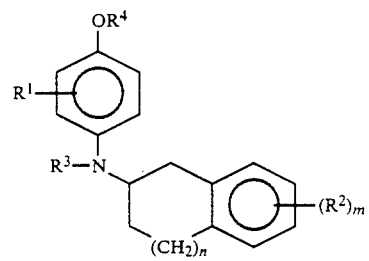

wherein m is 0, 1 or 2; n is 2 or 3; $R_1$ and $R^2$ may be the same or different and are H, hydroxy, or alkoxy; $R^3$ is H, lower alkyl, alkanoyl or aroyl; and $R^4$ is H, lower alkyl or alkanoyl, and including acid-addition salts thereof.

18. The compound having the name the decanoate ester of 4-[(2,3-dihydro-1H-inden-2-yl) methylamino]-phenol.

* * * * *